United States Patent [19]

Greene et al.

[11] Patent Number: 5,155,244

[45] Date of Patent: Oct. 13, 1992

[54] PREPARATION OF ANTIOXIDANT GLYCERIDE DERIVATIVES UTILIZING ESTERIFICATION

[75] Inventors: George H. Greene, Croton-Hudson, N.Y.; James C. Phillips, Plain City, Ohio; Jerry F. Stults, Ostrander, Ohio; Jan P. E. Tellings, Columbus, Ohio

[73] Assignee: Karlshamns AB, Sweden

[21] Appl. No.: 488,719

[22] Filed: Feb. 28, 1990

[51] Int. Cl.⁵ .................................................. G11B 5/00
[52] U.S. Cl. .......................................... 554/2; 554/4; 554/5; 554/7; 252/397; 252/399; 252/400.2; 252/400.21; 252/400.24; 252/401; 252/404; 252/405; 252/407; 560/3; 560/53; 560/57; 560/67; 560/70; 560/75
[58] Field of Search .................. 260/398.5, 403, 404, 260/404.5, 404.1, 410, 410.7, 410.8, 410.9; 560/3, 53, 54, 67, 70, 75; 252/397, 399, 400.2, 400.21, 400.24, 401, 404, 405, 407

[56] References Cited

U.S. PATENT DOCUMENTS

| | | | |
|---|---|---|---|
| 1,744,596 | 1/1930 | van Loon | 260/410.8 |
| 2,026,785 | 1/1936 | Harris | 260/403 |
| 2,558,547 | 6/1951 | Eckey | 260/410.7 |
| 2,614,937 | 10/1952 | Baur | 426/601 |
| 3,006,771 | 10/1961 | Babayan | 260/410.7 |
| 3,012,049 | 12/1961 | Bill | 260/410.9 |
| 3,153,659 | 10/1964 | King | 260/410.8 |
| 3,275,597 | 9/1966 | Mauz | 260/410.6 |
| 3,337,596 | 8/1967 | Thompson | 260/410.7 |
| 3,721,704 | 3/1973 | Dexter | 252/404 |
| 3,839,278 | 10/1974 | Dexter et al. | 260/398.5 |
| 4,093,587 | 6/1978 | Spivack | 260/398.5 |
| 4,196,134 | 4/1980 | Ball et al. | 260/404.8 |
| 4,209,451 | 6/1980 | Hameyer et al. | 260/410.8 |

Primary Examiner—Paul F. Shaver
Assistant Examiner—Deborah D. Carr
Attorney, Agent, or Firm—Burns, Doane, Swecker & Mathis

[57] ABSTRACT

A method of solubilizing a first compound in a second medium where the first compound has a limited solubility in the second medium. In particular, the method comprises reacting the first compound with the second medium. By this reaction, a product is formed whereby an active component of the first compound is covalently incorporated into the second medium.

The first compound and second medium each contain at least one reactive group which will react with a reactive group of the other. In addition, the first compound comprises at least one antioxidant which will be covalently bonded to and thus effectively solubilized in the second medium by the reaction.

The second medium comprises glyceride derivatives, silicones, fluorocarbons and alkoxylates containing reactive groups such as hydroxy, amino, carboxyl, ester, or amides.

19 Claims, No Drawings

PREPARATION OF ANTIOXIDANT GLYCERIDE DERIVATIVES UTILIZING ESTERIFICATION

BACKGROUND OF THE INVENTION

The present invention relates to a method of solubilizing a compound in a medium such as a lubricating composition.

The use of antioxidants as stabilizing materials for lubricant compositions employed with synthetic fibers is known in the art as a means to increase the thermal stability of the lubricant.

However, as process speeds for manufacturing these synthetic fibers have increased, the need for even greater thermal stability of the lubricant has become evident. Improved thermal stability would be effective in reducing the excessive volatility which is present at high temperature points within, for example, the drawing and heat setting processes.

In addition, a lubricant composition having a very high thermal stability would remain fluid at these high temperature process points. Accordingly, if the lubricant is sufficiently stable, any lubricant accumulation occurring at these points will be removed by the continuous wiping action as the fibers are processed. As a result, maintenance costs could be reduced and fiber quality could also be improved because deleterious frictional changes could be effectively eliminated.

As was previously noted, antioxidants are commonly used to enhance the thermal stability of lubricants. However, the need for even greater thermal stability necessitates very high concentrations of antioxidants in lubricant formulations.

Moderate levels of antioxidant can be achieved with compositions such as butylated hydroxytoluene (BHT). Unfortunately, BHT and similar antioxidants have substantial volatility at temperatures used to manufacture and process synthetic fiber. Consequently, this class of antioxidants volatilize rapidly and fail to prevent oxidation.

Other known phenolic antioxidants such as Irganox 1010 which have low volatility also have limited solubility in lubricant formulations. As a result, the requisite high antioxidant concentration cannot be effectively attained.

Thus, the need still exists for a method of increasing the solubility of compounds such as antioxidants in medium in which the compound have only limited solubility, i.e., lubricant compositions.

Accordingly, it is an object of the present invention to provide a method for solubilizing compounds in a medium.

It is a further object to provide a thermally stable lubricant/surfactant composition containing antioxidant groups.

It is still a further object of the present invention to provide lubricant/surfactant compositions which have antioxidant moieties covalently bonded into their structures in order to avoid excessive volatility as well as problems associated with limited solubility.

SUMMARY OF THE INVENTION

In accordance with the foregoing objectives, the present invention relates to a method of solubilizing a first compound in a second medium where the first compound has a limited solubility in the second medium. In particular, the method comprises the reacting of the first compound with the second medium. By this reaction, a product is formed whereby an active component of the first compound is covalently incorporated into the second medium.

Preferably, the first compound comprises an antioxidant which contains a group capable of reacting with a reactive group in the second component.

Furthermore, the second medium preferably comprises at least one compound having the following formula:

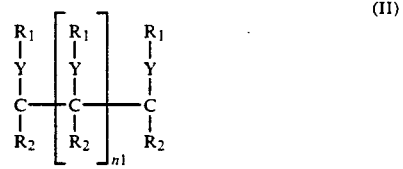

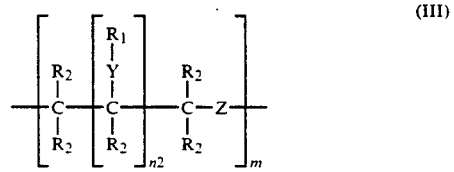

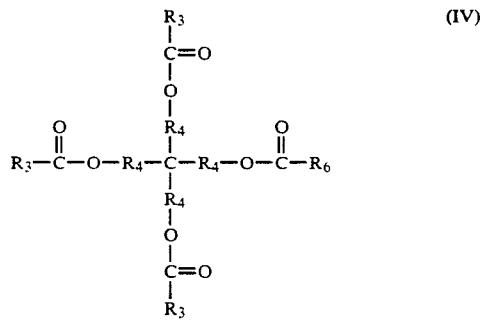

wherein Y can be the same or different and comprises

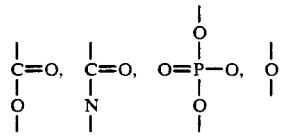

with the provisos that

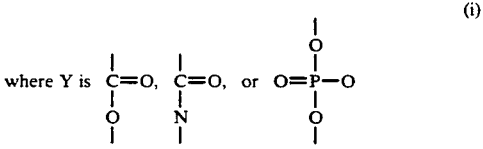

the corresponding $R_1$ group comprises
a cyclic or acyclic, an unsubstituted or a hydroxy, carboxy, or halogen substituted alkyl, alkenyl, alkynyl, or oxyalkylene group or a sulfur, nitrogen or phosphorus derivative of an alkyl, alkenyl, alkynyl, or oxyalkylene group, an unsubstituted or substituted aryl group, or mixtures thereof, and
(ii) where Y is

the corresponding $R_1$ group can be hydrogen, in addition to the above described compounds, with the further proviso that if Y is

and $R_1$ is not hydrogen, at least one of the Y groups in the compound is not

so that at least one of the $Y-R_1$ is reactive with the first compound;

and further wherein $R_2$ can be the same or different and comprises those $R_1$ groups described in proviso (ii) above, $R_3$ and $R_4$ can be the same or different and each comprise an alkyl group, Z can be an O, N, or P, $N1 = 0-20$, $n2 = 1-20$, and $m = 1-100$.

DETAILED DESCRIPTION OF THE PREFERRED EMBODIMENTS

The present invention relates to a method for solubilizing a first compound in a second medium in which the first compound would otherwise have only a limited solubility. In particular, the method of the present invention relates to the reaction of the first compound with the second medium so as to covalently incorporate the first compound into the second medium.

The first compound and second medium each contain at least one reactive group which will react with a reactive group of the other. Accordingly, the first compound will be covalently bonded to and thus effectively solubilized in the second medium by the reaction.

The first compound according to the present invention comprises at least one antioxidant which contains a reactive group capable of reacting with a reactive group in the second compound.

Preferably, the reactive group comprises $-CO_2R$, $-OH$, $-NR_2$, $-CNR$, or an oxyphosphorus residue wherein R is defined in the same manner as $R_2$ in the second compound.

In addition, the first compound preferably comprises di-tert-butyl-4-hydroxyhydrocinnamic (DTBH) acid and derivatives thereof, particularly esters, dialkyl or diaryl phosphonates, or trialkyl or triaryl phosphites, gallic acid and derivatives thereof, particularly ester derivatives such as propyl gallate, ascorbic acid and derivatives thereof, and citric acid and derivatives thereof, particulalry ester derivatives.

Specific examples of suitable first compounds include hindered phenolic antioxidants such as the Irganox series (Irganox is a trademark of Ciba-Geigy).

The second medium comprises at least one glyceride derivative, silicone, fluorocarbon and alkoxylate containing reactive groups such as hydroxy, amino, carboxyl, ester, or amides. Examples of suitable second compound include aminosilicones such as Shin-Etsu KF-393, fluorocarbons such as perfluoroalcohol started alkoxylates, and glyceride derivatives having the following formula:

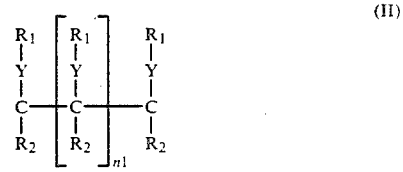
(II)

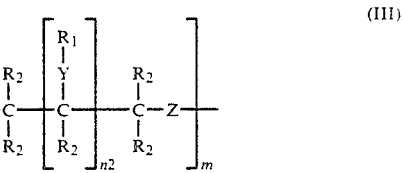
(III)

or

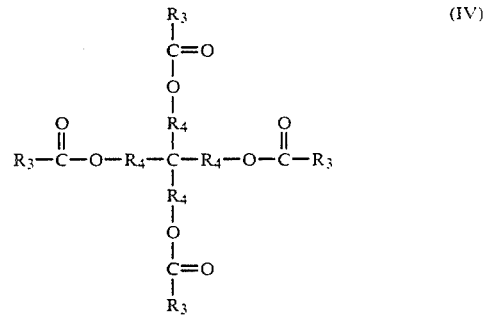
(IV)

wherein Y can be the same or different and comprises

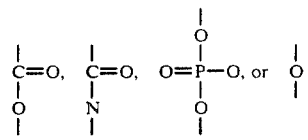

with the provisos that

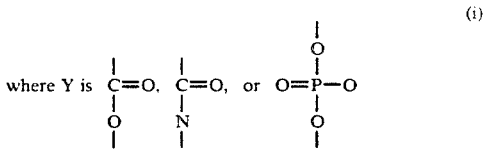
(i)

the corresponding $R_1$ group is cyclic or acyclic and comprises an unsubstituted or hydroxy, carboxy, or halogen substituted alkyl, alkenyl, alkynyl, oxyalkylene group; a sulfur, nitrogen or phosphorus derivative of the above alkyl, alkenyl, alkynyl, oxyalkylene groups; an unsubstituted or substituted aryl group; or mixtures thereof, and, (ii) where Y is $$\begin{array}{c} | \\ O. \\ | \end{array}$$

the corresponding $R_1$ group can be hydrogen, in addition to the above described compounds, with the further proviso that if all of the Y groups are $$\begin{array}{c} | \\ O. \\ | \end{array}$$

then at least one of the corresponding $R_1$ groups is hydrogen so that at least one of the combinations of Y-$R_1$ is reactive with the first compound.

In addition, $R_2$ can be the same or different and comprises those $R_1$ groups described in proviso (ii) above, $R_3$ comprises an alkyl group, $R_4$ comprises an alkyl group, Z can be an O, N, or P, $n1 = 0-20$, $n2 = 1-20$, and $m = 1-100$.

Specific examples of classes of compounds according to formula II include glycerides, amides, and phospholipids while classes of compounds according to formula III include polyglycerols.

The reaction conditions selected for the reaction between the first compound and the second medium are dependent upon the reactants chosen and the desired composition of the final product. For example, the greater the ratio between the first compound and the second medium, the more —$R_1$ or —$R_3$ groups which will be substituted with the antioxidant group.

Moreover, this reaction according to the present invention may optionally occur in the presence of a catalyst in order to facilitate the reaction between the first compound and second medium.

In this regard, the correlation between reactants, catalysts, reaction conditions and the final products would be easily determined by those skilled in the art and thus are not further discussed herein.

The present invention also relates to the reaction product formed by the reaction of the first compound and the second medium.

In this product, the first compound is covalently bonded to the second medium, thus allowing the first compound to be effectively solubilized into the second medium to a degree which otherwise would not be obtainable.

With respect to the preferred formulas above, this product is illustrated by formulas V, VI and VII below:

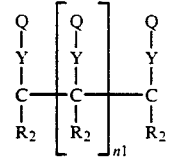

(V)

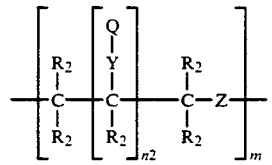

(VI)

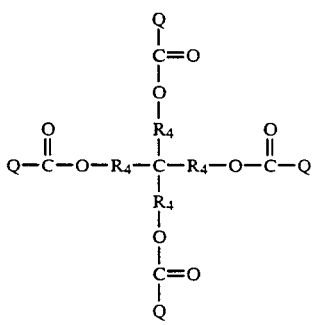

(VII)

In these formula Y, Z, $R_1$, $R_2$, $R_3$, $R_4$, n1, n2, and m are the same as defined above, and in formula (V) and (VI), Q comprises the first compound or —$R_1$ while in formula (VII), Q comprises the first compound or —$R_3$, with the further proviso that in each formula, at least one Q group comprises the first compound, i.e., an antioxidant.

Preferably, the first compound comprises DTBH acid, a dialkyl or diaryl phosphonite, or a trialkyl or triaryl phosphite. Y preferably comprises

and $R_2$ comprises hydrogen.

Moreover, $R_1$ preferably comprises coconut oil having a chain length of $C_6$-$C_{18}$ which is unsaturated to yield an I.V. of 7-12.

In a preferred embodiment of the present invention, the solubility of an antioxidant in a medium in which it has limited solubility, i.e. a lubricant, can be increased.

It is important to recognize that while the following discussion focuses upon the preferred embodiment of the invention, one of ordinary skill in the art would clearly recognize that this discussion is equally applicable to other embodiments of the invention.

In this embodiment, an antioxidant is employed as the first compound while glyceride derivatives corresponding to formula II to VI are preferably employed as the second medium.

The preferred antioxidants are those where the reactive group of the first compound is —COOR (i.e., an ester) or an oxyphosphorus residue.

When the reactive group is —COOR, the first compound comprises:

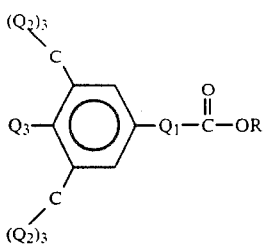

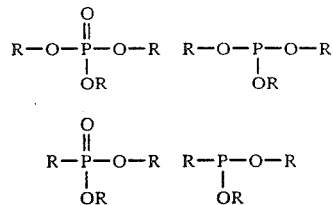

where $Q_1$ is an alkyl or an oxyalkylene group, $Q_2$ is H, or an alkyl group and $Q_3$ is —OH or —SH and the R group is an alkyl, aryl or alkyloxy group.

When the reactive group is defined as an oxyphosphorus group, the first, compound includes those phosphate, phosphite, phosphonite, and phosphinite compounds which are respectively illustrated below:

In each case the R group may be the same or different and comprises, aryl groups, alkyl groups, alkyloxy groups, oxyalkylene groups, or mixture thereof, which may be unsubstituted or substituted with hydroxy or groups containing sulfur or phosphorus atoms.

Examples of antioxidants which are employed with the present invention include sterically hindered phenols, as well as phosphonites, phosphites and sulfides. Specific compounds which can be employed include IRGANOX 1010, IRGANOX 1076, IRGANOX 259, IRGANOX 1098, IRGANOX 245 (IRGANOX is the trademark of Ciba-Geigy). Examples of these compounds are illustrated below. Irganox 1010

Irganox 1010

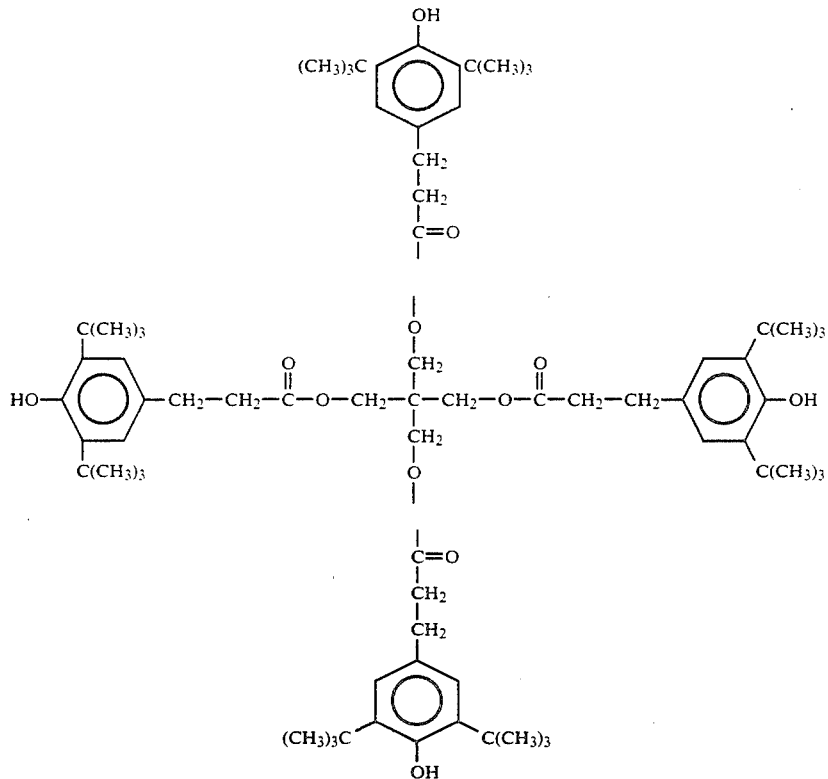

Irganox 1076

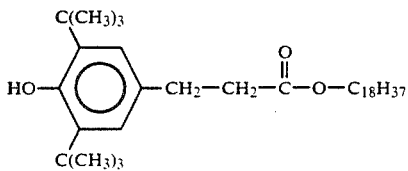

Irganox 1098

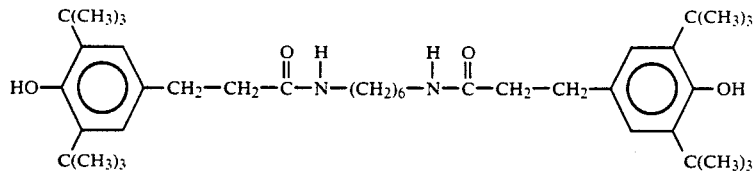

Irganox 245

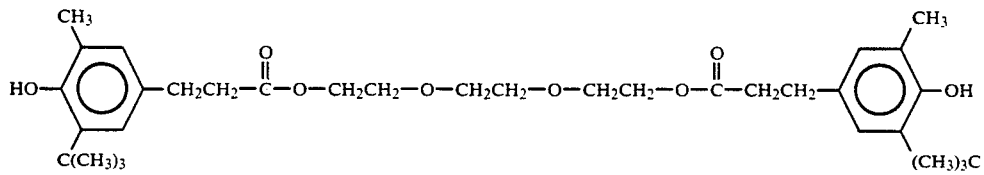

Irganox 259

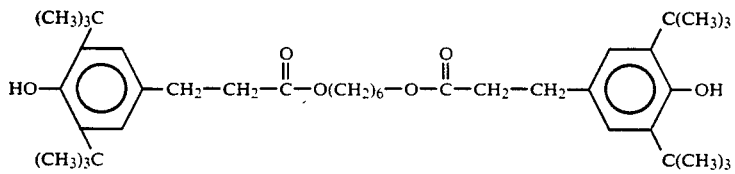

The glycerides which can be effectively employed as the second medium in the present invention include those glycerides and polyglycerols, polyols, and esters (both mono- and polyfunctional) which contain organic acid groups with carbon groups having chain lengths of $C_1$-$C_{50}$. In addition, these compositions may contain other groups such as polyoxyalkylene groups which are bonded to the carbon skeletal (e.g., glyceride) structure.

Specific examples of these compositions include those based on natural oils and their hydrogenated analogs, for example, palm kernel oil, canola oil, coconut oil, soybean oil, sunflower oil and high-oleic sunflower oil, castor oil, mink oil, shea oil, castor wax, other glycerides such as glycerol tripelargonate, glycerol trioleate, glycerol tricaproate, and other polyglycerol or polyol esters, including, for example, alkoxylated coconut oil, triglycerol dioleate, hexaglycerol dioleate, decaglycerol dioleate, trimethylol propane (or TMP)-tripelargonate, trimethylol ethane (or TME)-tripelargonate, TMP-tri-isostearate, TME-triisostearate, sorbitan oleates, stearates, and isostearates, pentaerythritol tetrapelargonate and propylene glycol diethylhexanoate, with coconut oil being the more preferred compound.

In this embodiment, a composition according to the present invention is provided by the reaction between the first compound and the second medium. This reaction is generally classified as either an interesterification, or transesterification reaction of a glyceride with an antioxidant, or a direct esterification reaction.

In either case, the antioxidant is preferably present in the reaction mixture in an amount which is effective in providing a "superstable lubricant" when the reaction is performed. This amount is greater than zero but preferably less than 30% by weight of the reaction mixture.

By the term "superstable lubricant" it is meant that the antioxidant contained therein does not salt out.

The stability of the lubricant can be illustrated by the time needed for the lubricant to polymerize, i.e., to change from a free-flowing liquid into a gel or a solid. The larger the value for the time to polymerization, the more stable the lubricant.

A "superstable lubricant" according to the present invention has a value of greater than about 150 minutes when upwards of 10% of the antioxidant is covalently bound into the lubricant.

It should be noted that such values are much greater than the less than 30 minute value associated with traditional lubricant compositions.

These values are based on "oven stability tests" of the lubricant. In this test, approximately 200 mg samples of lubricant is weighed into aluminum weigh pans and placing said pans in an oven (manufactured by Gruenberg) held at 250 degrees Centigrade ($+/-10$ degrees) until the lubricant sample has polymerized, i.e., the sample is no longer fluid.

In addition to the glyceride and antioxidant reactants, this embodiment preferably utilizes a catalytic material in order to promote the reaction.

The catalysts which are effective within this embodiment of the present invention are those known in the art and include sodium methylate, potassium hydroxide, and sodium hydroxide, and sodium/potassium metal alloy with sodium methylate being most preferred.

This catalyst is preferably present in an amount of about 0.02 to about 2 % by weight of the reactant materials with approximately 1% by weight being most preferred.

The glycerides (or other esters) are preferably present in an amount greater than about 40% by weight of the reaction mixture, with about 90% by weight of the reaction mixture being more preferred.

The rearrangement or transesterification reaction can be performed by any known method within the art such as those described within Bailey's Industrial Oil and Fat Products.

For example, a batch process can be employed where the triglyceride and the antioxidant are mixed together in a vacuum and heated to a temperature of about 90° C. to about 105° C. Then, while still under vacuum, the catalytic material is added and mixed into the reaction mixture. The vacuum can be removed as mixing is continued. The product is then heated, filtered, bleached and deodorized.

The resulting product is an antioxidant glyceride derivative which contains up to about 20% by weight of an antioxidant. As can be plainly seen, this solubility is much greater than the about 1% solubility which can be obtained by traditional methods.

In another method according to the invention, the above described antioxidant glyceride derivatives can be made through a direct esterification reaction.

In this aspect of the invention, the polyglycerols (i.e., second medium) are reacted with the first compound which comprises certain acids such as pelargonic acid, coconut fatty acids, and the like as well as hindered-phenolic acids such as DTBH (di-tert-butyl-4-hydroxyhydrocinnamic acid). Such direct esterification processes are also well known in the art and are not further described herein.

These compounds can be used as a lubricant for either natural, e.g., proteinaceous or natural cellulosic fibers, or synthetic fibers, e.g., polyesters, nylons, polypropylene, acrylic, aramid, or synthetic cellulosic fibers.

These compounds according to the present invention can be applied to a fiber in any conventional method known in the art, such as those described within U.S. Pat. Nos. 3,853,607; 4,390,591; and Proffitt and Patterson (JAOCS, Vol. 65, No. 10, 1988) which are incorporate herein by reference.

As a consequence of their exceptional thermal stability, these preferred antioxidant derivatives may also find utility as lubricants for internal combustion engines, gear boxes, transmissions and the like. For these uses, they may be formulated with selected oils, glycerides and various esters, detergents, and extreme pressure additives which are recognized in the art.

These compositions are particularly desirable with two-stroke engines because of their biodegradability. As a result, two-stroke engines lubricated with the subject compositions are environmentally sensitive when used in waterways, lakes, and impoundments when used to propel water craft. Similarly, use of these compositions as chain saw lubricants are expected to have less effect on the environment if a spill or leakage occurs.

Because of the combination of high temperature stability and biodegradability, these compositions can be employed as hydraulic fluids and power transmission fluids for earth moving equipment and the like. Similarly, these compositions can be employed as cutting lubricants used in the machining of metal parts. For such an application, the subject compositions may be formulated with surfactants to facilitate emulsification.

Because of very high temperature requirements, the compositions of the present invention can be employed as solder assist fluids. Solder assist fluids are used in the fabrication of circuit boards and require very high temperature stability because of prolonged exposure to molten solder. In such an application, the composition would contain antioxidant and sufficient polyoxyalkylene to make the subject composition either water dispersible or water soluble. This would allow cleansing of circuit boards with water instead of solvents which must be carefully recovered to avoid environmental contamination.

Additionally, these compositions according to the present invention can be employed as heat exchange fluids for high temperature applications.

In order to further illustrate the present invention, and the advantages thereof, the following specific examples are given. It being understood that same are intended solely as illustrative and in no way limitive.

EXAMPLES

EXAMPLE 1

Preparation by Trans- or Inter-esterification

The following procedure illustrates the interesterification of Irganox 1010 with triglycerides or other esters. The Irganox 1010 and the oil was charged into a three necked round bottom flask with a nitrogen inlet, outlet, thermometer and agitator. The charge was heated to 110°-120° C. under nitrogen to remove water (typically for 20 minutes). The charge was cooled to approximately 90° C. Sodium methoxide was then added slowly. The amount is usually approximately 0.2% for low acid value oils. More sodium methoxide was required for high acid value oils. When sufficient sodium methoxide was added to the reaction, the charge turned red-brown in color and the smell of methyl esters was noted. If the charge did not turn red-brown, then there was not enough sodium methoxide in the batch. The reaction was held at 90°-110° C. for approximately one hour. Concentrated phosphoric acid (85%) was then added dropwise until the color became lighter. The amount of acid was usually around three quarters of the weight of sodium methoxide added. The batch was then water washed 3-4 times until the wash water remained at a pH of 5-6. The batch was then bleached and deodorized.

Example A 900.0 g High oleic sunflower oil
100.0 g Irganox 1010
enough sodium methoxide was added to change color and enough phosphoric acid was added to reverse color.

Example B 1400.0 g pentaerythritol tetrapelargonate
155.6 g Irganox 1010
3.9 g sodium methoxide
later 3.5 g 85% phosphoric acid Example C 1600.0 g glycerol tripelargonate
177.8 g Irganox 1010
4.4 g sodium methoxide
later 3.9 g 85% phosphoric acid Example D 270.0 g RBF 76° coconut oil
30.0 g Irganox 1010
enough sodium methoxide was added to change color and enough phosphoric acid to reverse color.

EXAMPLE 2

Preparation by Direct Esterification

A procedure for making esters from 3,5-di-tert-butyl-4-hydroxyhydrocinnamic acid (DTBH acid), fatty acids and polyol is as follows. The DTBH acid, appropriate fatty acids and desired alcohol is charged into a three necked round bottom flask. The flask is fitted with an agitator, thermometer, nitrogen inlet, and a reflux condenser topped with a condenser and a receiver. The charge is heated under a continuous flow of nitrogen until water begins to collect in the receiver (typically around 180° C.). The reaction is held at 180°-200° C. for 3-4 hours, then the temperature is raised to 235°-255° C. and held until the acid value is below 2.0 (usually 4-5 hours). The product is then cooled, bleached and deodorized.

Example E 278.4 g DTBH acid (1.0 mole)
2505.6 g pelargonic acid (15.9 moles)
573.6 g pentaerythritol (4.2 moles)
on GLC-FAC assay, this composition would show approximately 10% DTBH acid and 90% pelargonic acid.

Example F 278.4 g DTBH acid (1.0 mole)
2505.6 g Oleic acid (8.9 moles)
303.8 g 99.9% glycerol (3.3 moles)
on GLC-FAC assay, this composition would show approximately 10% DTBH acid and 90% oleic acid.

Example G 62.7 g DTBH acid (0.23 moles)
564.0 g Oleic acid (2 moles)
462 g hexaglycerol (1 mole)
on GLC-FAC assay, this composition would show about 10% DTBH and 90% Oleic acid.

EXAMPLE 3

Direct Esterification

A three necked 250 ml round bottom flask equipped with a motor driven stirrer and distillation setup is charged with 90 g of perfluoroalcohol started eithylene oxide polymer and 10 g of DTBH acid. The reaction mixture is heated at 150° C. for 8 hours under a blanket of nitrogen. The progress of the reaction is monitored by the distillation of water and infrared spectroscopy.

EXAMPLE 4

Interesterification

A three neck round bottom flask (250 ml) equipped with a mechanical stirrer is charged with 90 g of a perfluoroalcohol started ethylene oxide polymer and 10 g of Irganox 1010. The mixture is blanketed with nitrogen and 1 g of sodium methoxide is added as catalyst. The reaction mixture is heated to 150° C. and the temperature is maintained for 1 hour. The mixture is neutralized with phosphoric acid and the volatiles removed under reduced pressure.

EXAMPLE 5

Comparative Results

The following comparative Tables illustrate the improvement in performance achieved with the present invention.

PERFORMANCE OF HIGH TEMPERATURE LUBRICANTS WITH OVEN TEMPERATURE MAINTAINED AT 250° C. (METHOD B)

| Composition | Polymerization Time (minutes) | % Residue | Acetone % Residue |
| --- | --- | --- | --- |
| coconut oil* | <30 | 17.6 | 17.7 |
| pentaerythritol | <30 | 21.0 | 20.4 |
| 4-pelargonate* glycerol tri-pelargonate* | <30 | 6.5 | 6.5 |
| coconut oil/ Irganox 1010 (1) | 210 | 24.1 | 19.6 |
| pentaerythritol 4-pelargonate/ Irganox 1010 (1) | 296 | 28.3 | 0.6 |
| glycerol tri-pelargonate/ Irganox 1010 (1) | 151 | 2.1 | 0.0 |
| coconut oil/ Irganox 1076 (1) | 153 | 26.5 | 25.0 |
| coconut oil/ Irganox 1076 (2) | 253 | 21.5 | 18.8 |
| Dimethyl-silicone (3)* | 254 | 97 | 97 |

*comparative example
(1) composition contains ten weight percent antioxidant
(2) composition contains twenty weight percent antioxidant
(3) UC Brand L-45; 50 CST The % Residue is the material remaining after thermal treatment in a Gruenberg oven.

Acetone is used to simulate process clean-up. Acetone % Residue is the material remaining after a triple acetone rinse/drying.

In both cases low residue is desirable. The use of the Irganox raises % Residue somewhat but not to an undesirable level. In all but one example, the presence of Irganox lowers Acetone % Residue. This is extremely desirable because easily removable residue facilitates clean-up of heater plates and other parts of the machinery used to manufacture fiber. Improvement in Acetone % Residue suggests that Irganox has impeded oxidatively induced crosslinking.

Clearly, the presence of Irganox effects a very major improvement in thermal stability as evidenced by much longer polymerization times. The control values are listed as less than thirty minutes because of the difficulty in determining lower values.

This test utilizes a standard laboratory oven made by Gruenberg. Determination of the end point requires that the oven's door must be opened to see if the experimental sample has gelled. Because the oven temperature must stabilize, low polymerization times at this temperature can be inaccurate.

Pentaerythritol tetrapelargonate is considered to be an industry standard for high temperature lubricant applications. Accordingly, the fact that coconut oil/Irganox derivative is at least seven times more stable, while the pentaerythritol/Irganox derivative is at least ten times more stable illustrates the advantages which can be associated with the present invention.

While the present invention has been described in terms of various preferred embodiments, the skilled artisan will appreciate that various modifications, substitutes, omissions, and changes may be made without departing from the spirit thereof. Accordingly it is intended that the scope of the present invention be limited solely by the scope of the following claims including equivalents thereof.

What is claimed is:

1. A method for producing an antioxidant derivative comprising reacting a first compound with a second medium in the presence of a catalyst wherein the first compound is an antioxidant containing a group capable of reacting with a reactive group in the second medium and the second medium is at least one compound having the following formula:

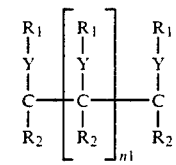 (II)

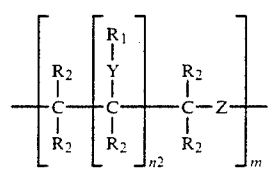 (III)

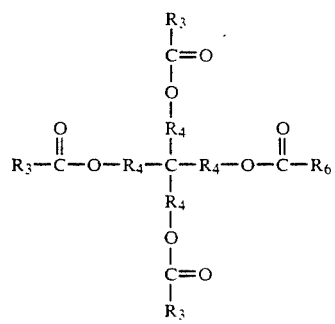 (IV)

wherein Y can be the same or different and comprises

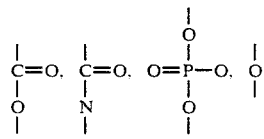

with the provisos that (i) where Y is 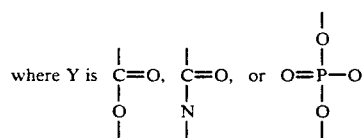

the corresponding $R_1$ group comprises
a cyclic or acyclic, an unsubstituted or a hydroxy, carboxy, or halogen substituted alkyl, alkenyl, alkynyl, or oxyalkylene group or a sulfur, nitrogen or phosphorus derivative of an alkyl, alkenyl, alkynyl, or oxyalkylene group, an unsubstituted or substituted aryl group, or mixtures thereof,
and
(ii) where Y is

the corresponding $R_1$ group can be hydrogen, in addition to the above described compounds, with the further proviso that if Y is

and $R_1$ is not hydrogen, at least one of the Y groups in the compound is not

so that at least one of the $Y-R_1$ is reactive with the first compound;
and further wherein $R_2$ can be the same or different and comprises those $R_1$ groups described in proviso (ii) above,
$R_3$ and $R_4$ can be the same or different and each comprise an alkyl group,
Z can be an O, N, or P,
n1 = 0-20,
n2 = 1-20, and
m = 1-100.

2. The method of claim 1 wherein the reactive group is the first compound comprises $-CO_2R$, $-OH$, $-NR_2$, $-CNR$, or any oxyphosphorus residue wherein R is defined in the same manner as $R_2$.

3. The method according to claim 1 wherein the first compound has the formula:

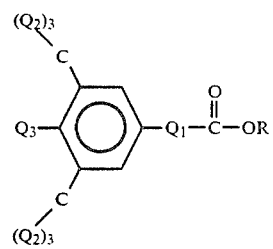

where $Q_1$ is an alkyl or an oxyalkylene group, $Q_2$ is H, or an alkyl group and $Q_3$ is $-OH$ or $-SH$ and R is an alkyl, aryl or alkyloxy group.

4. The method according to claim 1 wherein the first compound comprises:

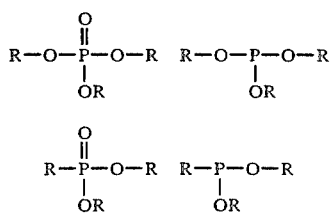

wherein each R group may be the same or different and comprises an aryl group, alkyl group, oxyalkylene group, or mixtures thereof which may be unsubstituted or substituted with hydroxy or groups containing sulfur or phosphorus atoms.

5. The method of claim 1 wherein the first compound comprises a phosphonate, a phosphite, a sulfide, gallic acid, derivatives of gallic acid, derivatives of ascorbic acid, citric acid or derivatives of citric acid.

6. The method according to claim 1 wherein the first compound comprises:

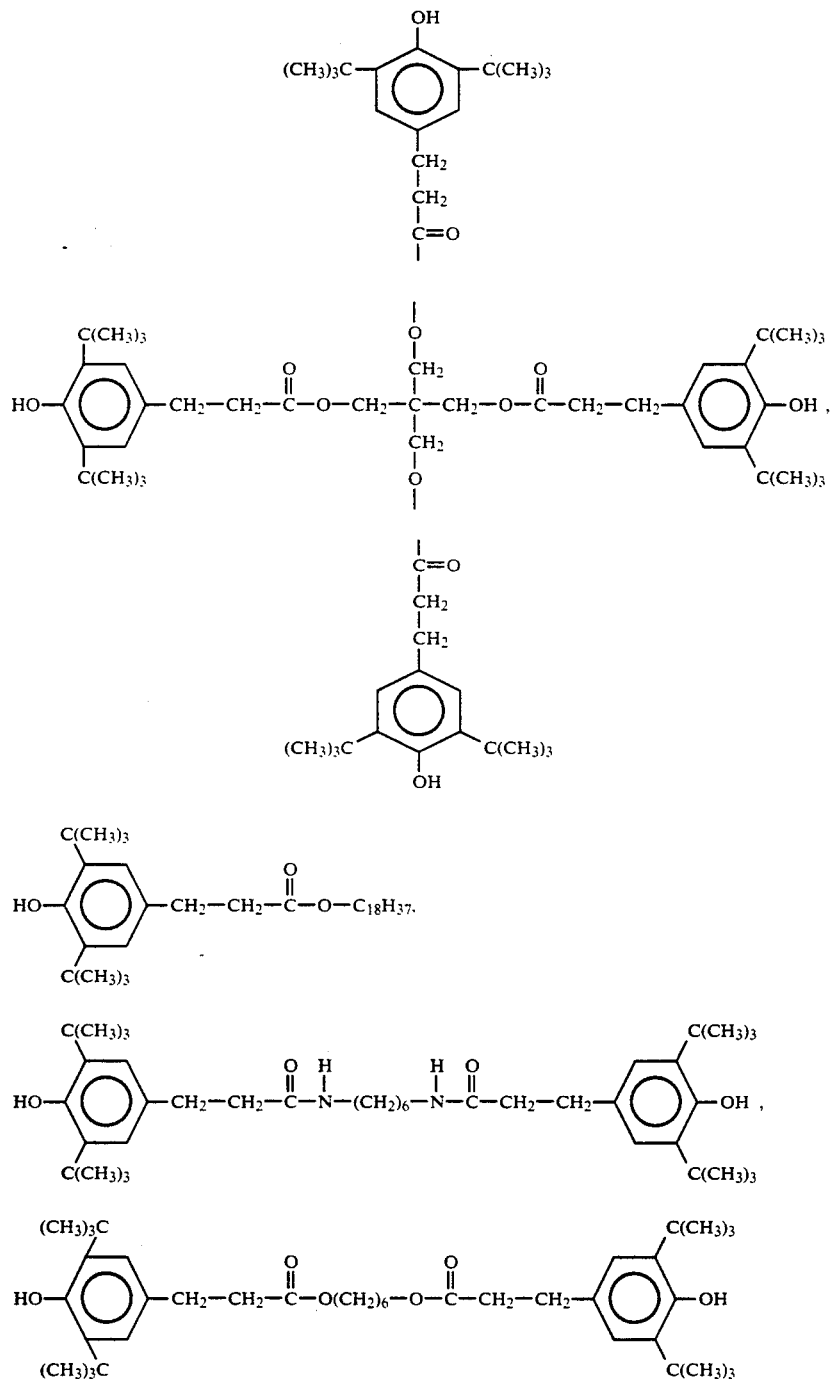

or,

-continued

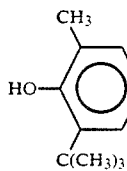 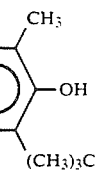

7. The method of claim 1 wherein the second medium comprises a glyceride, an amide, a phospholipid or mixtures thereof.

8. The method of claim 1 wherein the second medium comprises palm kernel oil, canol oil, coconut oil, soybean oil, sunflower oil and high-oleic sunflower oil, castor oil, mink oil, shea oil, castor wax, glycerol tripelargonate, glycerol trioleate, glycerol tricaproate, alkoxylated coconut oil, triglycerol dioleate, hexaglycerol dioleate, decaglycerol dioleate, TMP-tripelargonate, TME-tripelargonate, TMP-tri-isostearate, TME-tri-isostearate, sorbitan oleates, stearates, and isostearates, pentaerythritol tetrapelargonate, propylene glycol diethylhexanoate, or mixtures thereof.

9. The method of claim 1, wherein the second medium is a glyceride and wherein the antioxidant is present in an amount which is effective to provide a superstable lubricant.

10. The method according to claim 9 wherein the first compound comprises

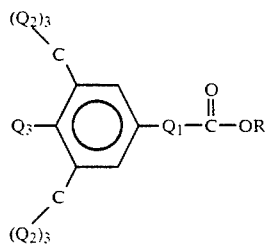

where $Q_1$ is an alkyl or an oxyalkylene group, $Q_2$ is H, or an alkyl group and $Q_3$ is —OH or —SH and R is an alkyl, aryl, or alkyloxy.

11. The method of claim 9 wherein the glyceride comprises palm kernel oil, canola oil, coconut oil, soybean oil, sunflower oil and high-oleic sunflower oil, castor oil, mink oil, shea oil, castor wax, glycerol tripelargonate, glycerol trioleate, glycerol tricaproate, alkoxylated coconut oil, triglycerol dioleate, hexaglycerol dioleate, decaglycerol dioleate, TMP-tripelargonate, TME-tripelargonate, TMP-tri-isostearate, TME-tri-isostearate, sorbitan oleates, stearates, and isostearates, pentaerythritol tetrapelargonate, propylene glycol diethylhexanoate, or mixtures thereof.

12. The method of claim 9, wherein the first compound is present in the reactant mixture in an amount greater than 0 but not greater than 20% by weight.

13. The method of claim 9 wherein the first compound is present in the mixture in an amount greater than 0 but not greater than 10% by weight.

14. The method of claim 10, wherein the first compound and second compound are selected such that the reaction is a transesterification reaction.

15. The method according to claim 14 wherein the first compound comprises:

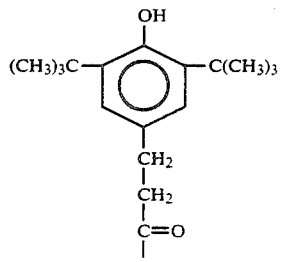

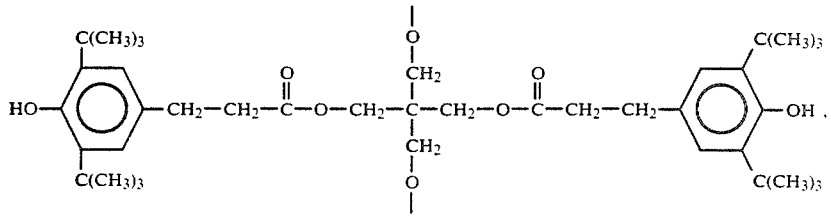

-continued

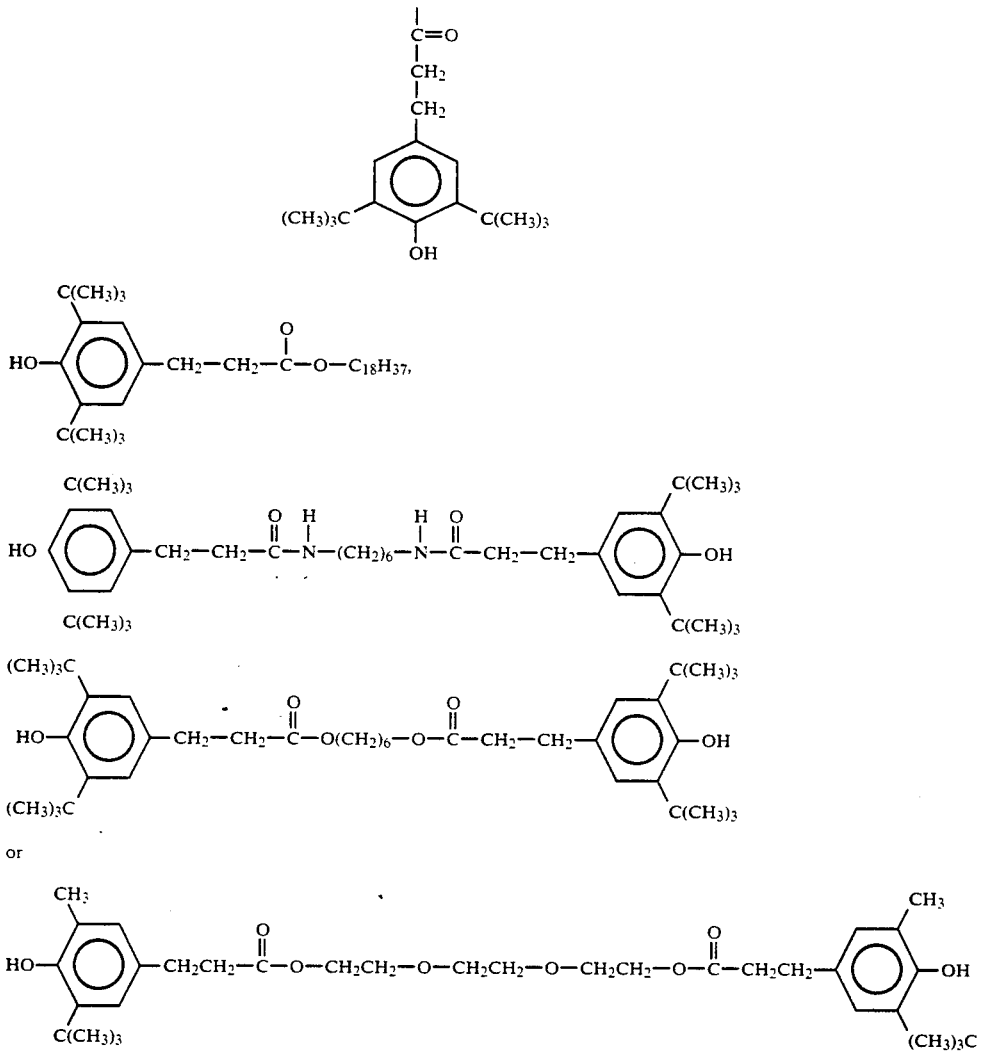

16. The method according to claim 1 wherein the catalyst comprises sodium methylate, potassium hydroxide or sodium hydroxide, sodium potassium metal alloy, or calcium oxide.

17. The method according to claim 1 wherein the catalyst is present in an amount of 0.2-2% by weight of the reactant mixture.

18. The method according to claim 9 wherein the first compound and the second medium are selected such that the reaction is a direct esterification reaction.

19. The method according to claim 18 wherein the first compound comprises 3,5-di-tert-butyl-4-hydroxyhydrocinnamnic (DTBH) acid.

* * * * *

UNITED STATES PATENT AND TRADEMARK OFFICE
CERTIFICATE OF CORRECTION

PATENT NO. : 5,155,244
DATED : October 13, 1992
INVENTOR(S) : George H. Greene et al Page 1 of 10

It is certified that error appears in the above-identified patent and that said Letters Patent is hereby corrected as shown below:

Column 2, lines 10-17,

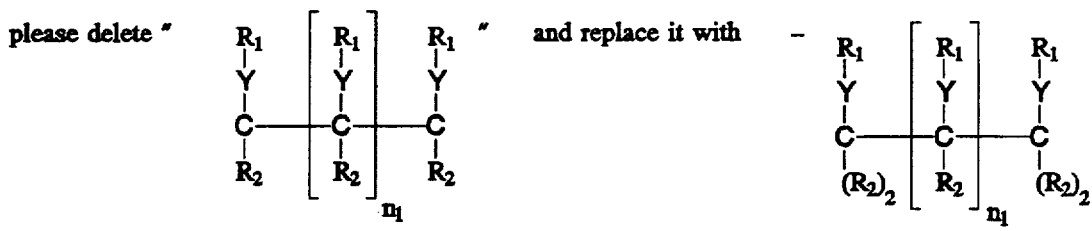

Column 2, lines 42-47

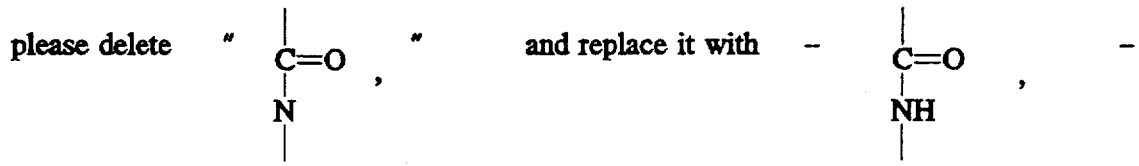

Column 2, lines 52-57

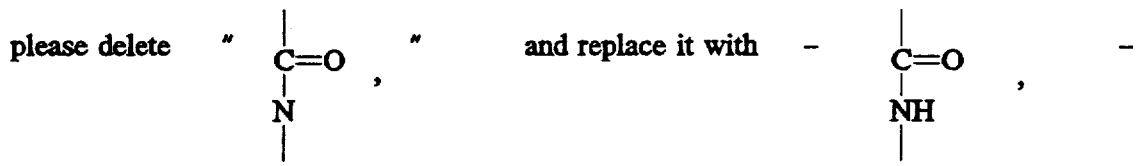

UNITED STATES PATENT AND TRADEMARK OFFICE
CERTIFICATE OF CORRECTION

PATENT NO. : 5,155,244
DATED : October 13, 1992
INVENTOR(S) : George H. Greene et al It is certified that error appears in the above-indentified patent and that said Letters Patent is hereby corrected as shown below:

Column 4, lines 13-20

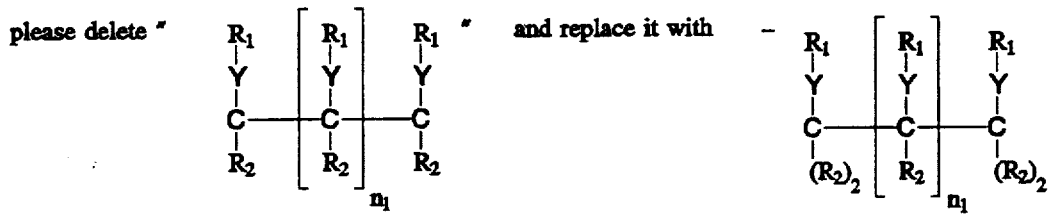

Column 4, lines 47-50

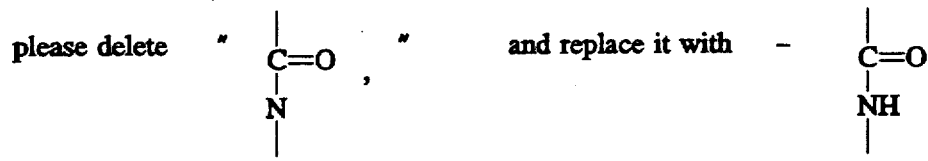

Column 4, lines 57-60

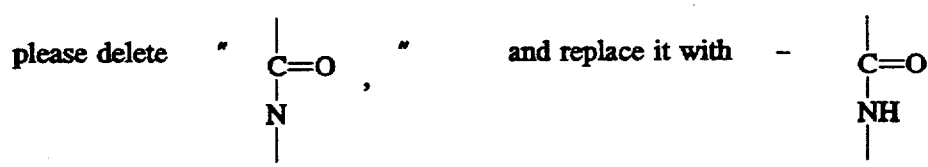

UNITED STATES PATENT AND TRADEMARK OFFICE
CERTIFICATE OF CORRECTION

PATENT NO. : 5,155,244
DATED : October 13, 1992
INVENTOR(S) : George H. Greene et al Page 3 of 10

It is certified that error appears in the above-indentified patent and that said Letters Patent is hereby corrected as shown below:

Column 6, lines 1-8, please delete
$$\begin{array}{c} Q \\ | \\ Y \\ | \\ C \\ | \\ R_2 \end{array} \left[ \begin{array}{c} Q \\ | \\ Y \\ | \\ C \\ | \\ R_2 \end{array} \right]_{n_1} \begin{array}{c} Q \\ | \\ Y \\ | \\ C \\ | \\ R_2 \end{array}$$

and replace it with
$$\begin{array}{c} Q \\ | \\ Y \\ | \\ C \\ | \\ (R_2)_2 \end{array} \left[ \begin{array}{c} Q \\ | \\ Y \\ | \\ C \\ | \\ R_2 \end{array} \right]_{n_1} \begin{array}{c} Q \\ | \\ Y \\ | \\ C \\ | \\ (R_2)_2 \end{array}$$

UNITED STATES PATENT AND TRADEMARK OFFICE
CERTIFICATE OF CORRECTION

PATENT NO. : 5,155,244
DATED : October 13, 1992
INVENTOR(S) : George H. Greene et al Page 4 of 10

It is certified that error appears in the above-indentified patent and that said Letters Patent is hereby corrected as shown below:

Columns 7 and 8, please delete

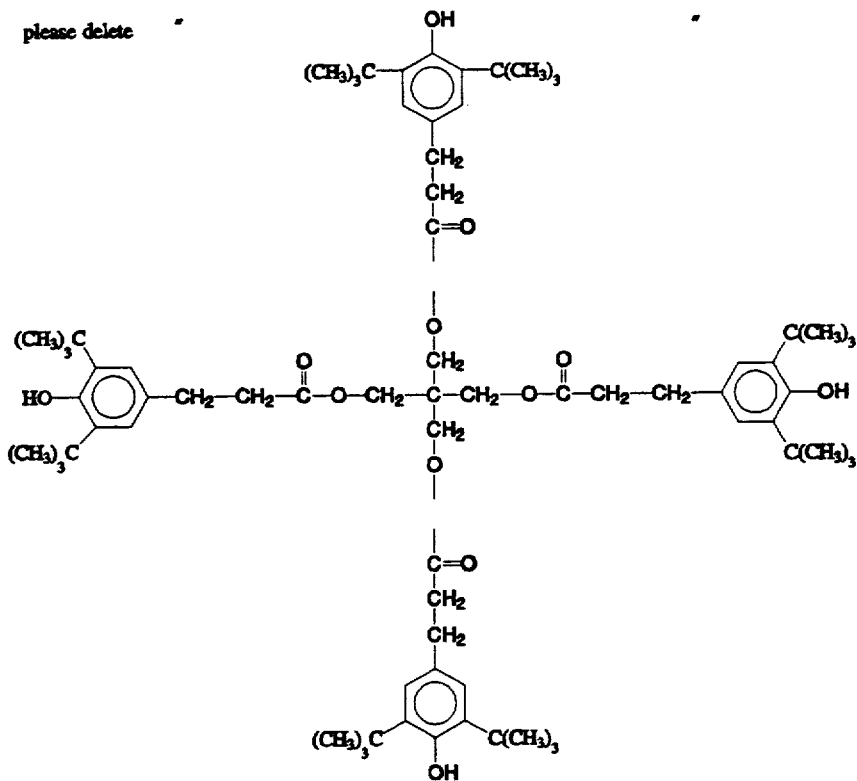

UNITED STATES PATENT AND TRADEMARK OFFICE
CERTIFICATE OF CORRECTION

PATENT NO. : 5,155,244
DATED : October 13, 1992
INVENTOR(S) : George H. Greene et al It is certified that error appears in the above-indentified patent and that said Letters Patent is hereby corrected as shown below:

and insert --

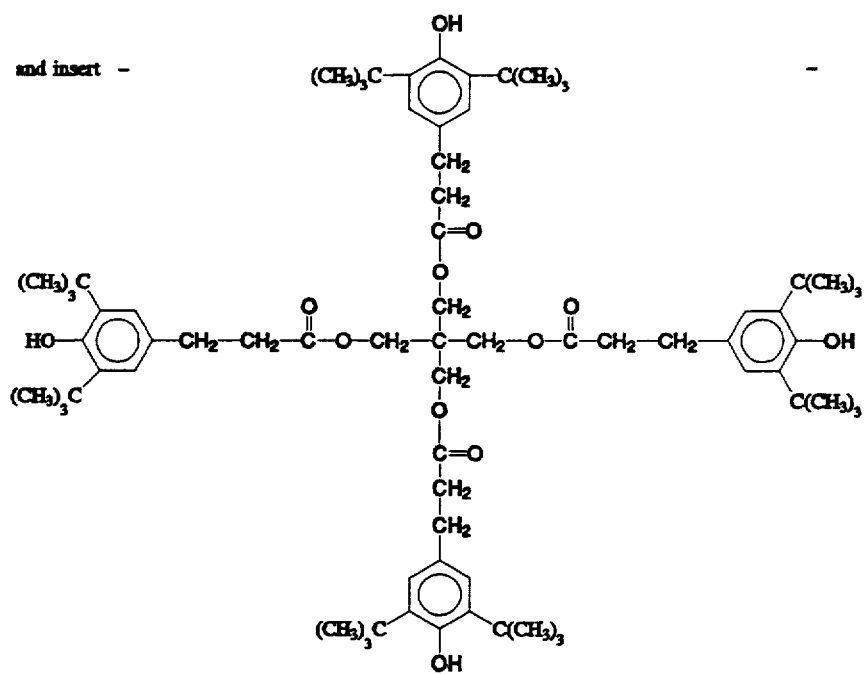

--

UNITED STATES PATENT AND TRADEMARK OFFICE
CERTIFICATE OF CORRECTION

PATENT NO. : 5,155,244
DATED : October 13, 1992
INVENTOR(S) : George H. Greene et al It is certified that error appears in the above-identified patent and that said Letters Patent is hereby corrected as shown below:

Column 7, line 17, please delete "," second occurrence.

Column 8, line 24, please delete "Irganox 1010".

Claim 1, column 15, lines 10-15 please delete " 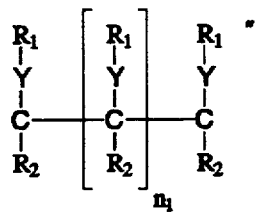 " and replace it with - 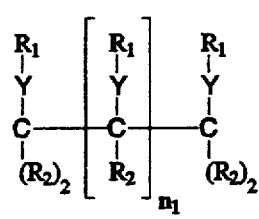 -

Claim 1, column 15, lines 40-45 and 52-56:

please delete " 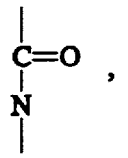 " and replace it with - 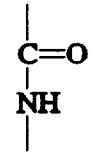 -

UNITED STATES PATENT AND TRADEMARK OFFICE
CERTIFICATE OF CORRECTION

PATENT NO. : 5,155,244
DATED : October 13, 1992
INVENTOR(S) : George H. Greene et al Page 7 of 10

It is certified that error appears in the above-indentified patent and that said Letters Patent is hereby corrected as shown below:

Claim 6, columns 17 and 18 please delete

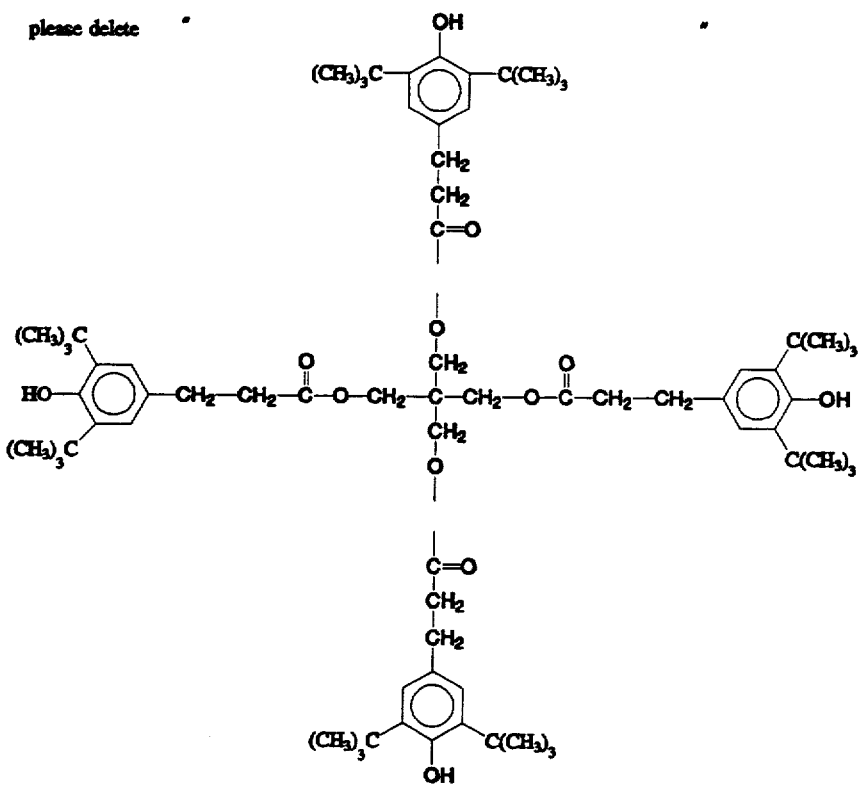

UNITED STATES PATENT AND TRADEMARK OFFICE
CERTIFICATE OF CORRECTION

PATENT NO. : 5,155,244
DATED : October 13, 1992
INVENTOR(S) : George H. Greene et al It is certified that error appears in the above-indentified patent and that said Letters Patent is hereby corrected as shown below:

and insert –

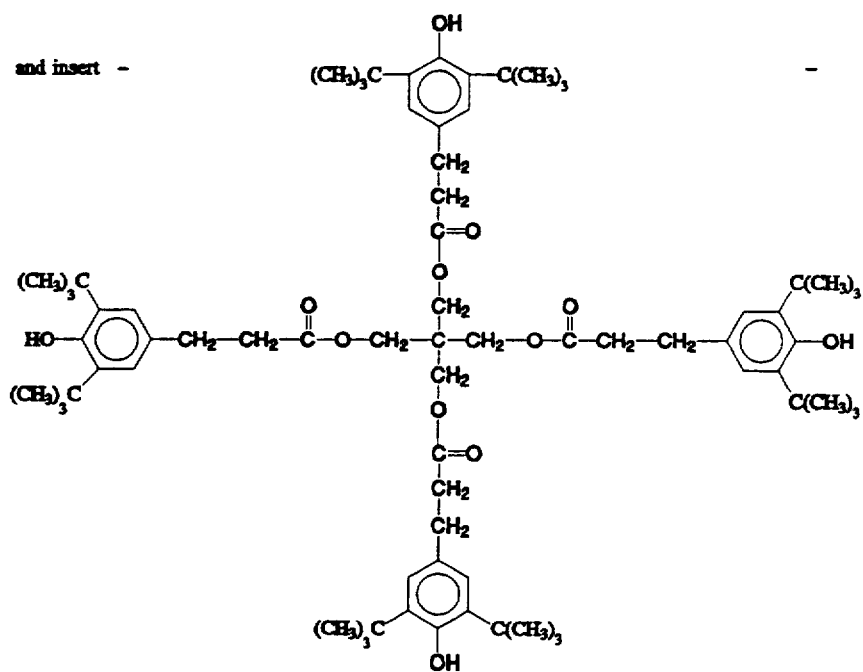

–

UNITED STATES PATENT AND TRADEMARK OFFICE
CERTIFICATE OF CORRECTION

PATENT NO. : 5,155,244
DATED : October 13, 1992
INVENTOR(S) : George H. Greene et al It is certified that error appears in the above-indentified patent and that said Letters Patent is hereby corrected as shown below:

Claim 15, columns 20 and 21, please delete

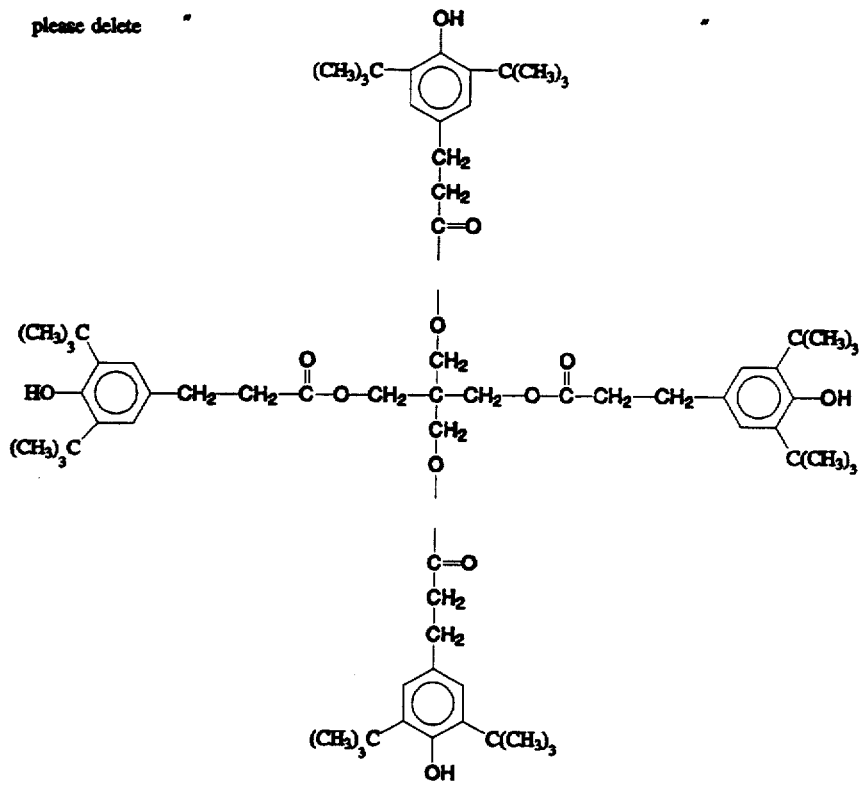

please delete

UNITED STATES PATENT AND TRADEMARK OFFICE
CERTIFICATE OF CORRECTION

PATENT NO. : 5,155,244
DATED : October 13, 1992
INVENTOR(S) : George H. Greene et al Page 10 of 10

It is certified that error appears in the above-indentified patent and that said Letters Patent is hereby corrected as shown below:

and insert -

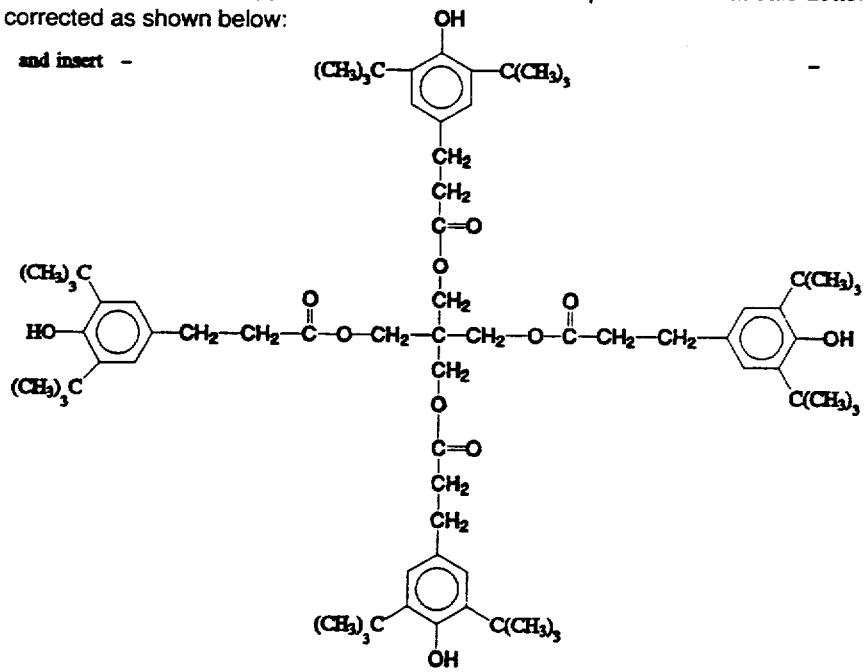

-

Signed and Sealed this

Thirteenth Day of September, 1994

Attest:

BRUCE LEHMAN

Attesting Officer

Commissioner of Patents and Trademarks